United States Patent [19]

LeMay

[11] 4,206,360
[45] * Jun. 3, 1980

[54] RADIOGRAPHY

[75] Inventor: Christopher A. G. LeMay, Osterley, England

[73] Assignee: E M I Limited, Hayes, Middlesex, England

[ * ] Notice: The portion of the term of this patent subsequent to Jan. 3, 1995, has been disclaimed.

[21] Appl. No.: 798,124

[22] Filed: May 18, 1977

Related U.S. Application Data

[63] Continuation of Ser. No. 559,715, Mar. 19, 1975, Pat. No. 4,066,902.

[51] Int. Cl.² .............................................. G03B 41/16
[52] U.S. Cl. .................................. 250/445 T; 250/360
[58] Field of Search ............... 250/445 T, 358 R, 359, 250/360

[56] References Cited

U.S. PATENT DOCUMENTS 3,866,047  2/1975  Hounsfield ..................... 250/445 T Primary Examiner—Craig E. Church
Attorney, Agent, or Firm—Cooper, Dunham, Clark, Griffin & Moran

[57] ABSTRACT

Radiographic apparatus utilizing a plurality of radiation-sensitive detectors to quantify the radiation emerging from a body along respective paths is provided with means for compensating for differences between the sensitivities of the various detectors. The compensating means includes an arrangement for displacing the source of the radiation relative to the detectors and for utilizing output signals obtained from one detector when the source is in its undisplaced and displaced positions respectively to predict what the output of a second detector, closely adjacent the first, should be if the sensitivities of the two detectors were equal. By comparing the prediction with the actual output signal provided by the second detector, differences in sensitivity are evaluated and allowed for. A technique for convolving difference signals rather than net signals is also disclosed.

9 Claims, 11 Drawing Figures

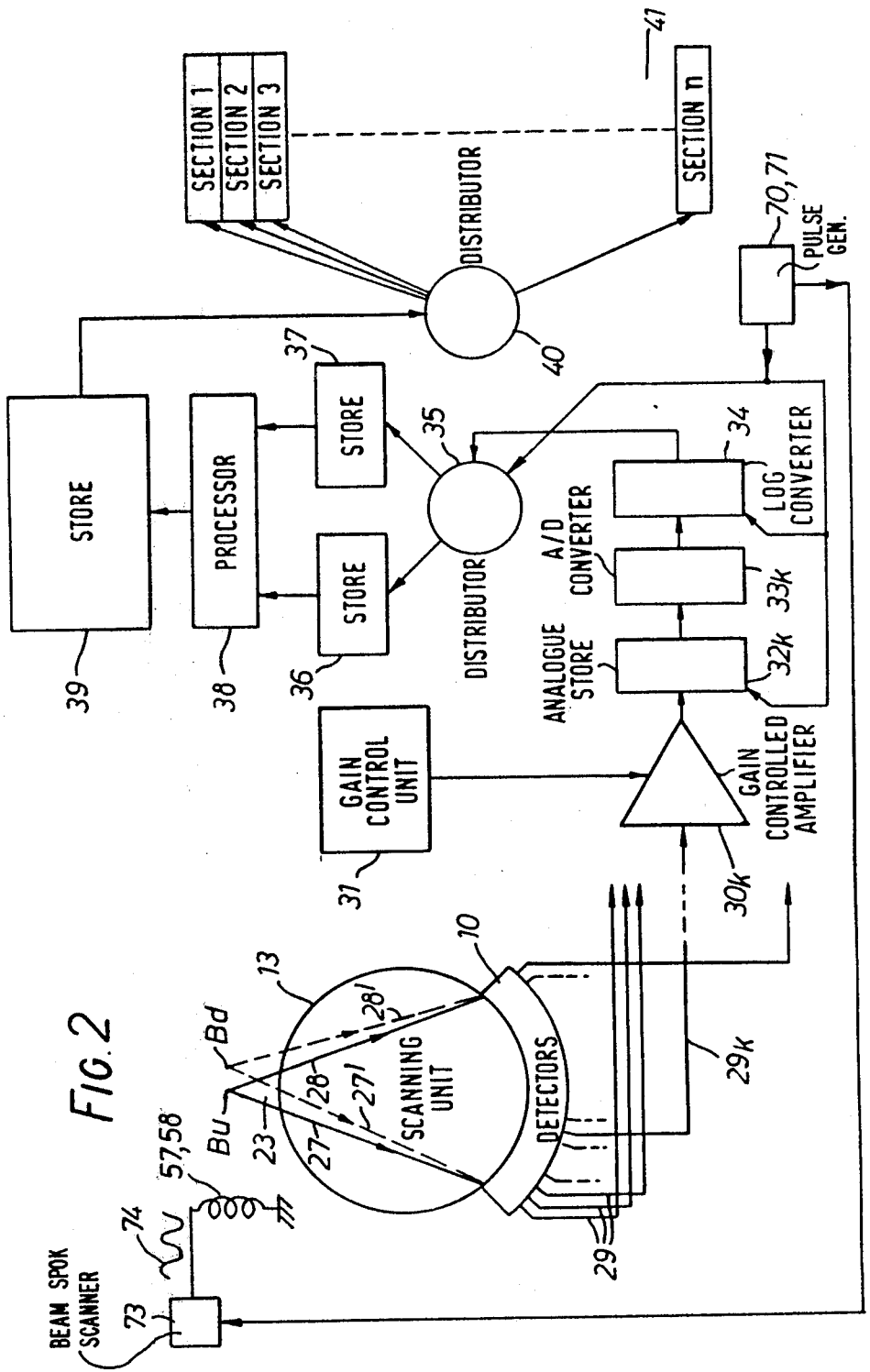

RADIOGRAPHY

This is a continuation of application Ser. No. 559,715 filed Mar. 19, 1975 now U.S. Pat. No. 4,066,902.

This invention relates to a method of and apparatus for examining a body by means of radiation such as X or γ-radiation.

The method and apparatus according to the invention can be used to assist in the production of radiographs in any convenient form, such as a picture on a cathode ray tube or other image forming device, a photograph of such a picture, or a map of absorption co-efficients such as may be produced by digital computer and on which contours may be subsequently drawn.

In the method of, and apparatus for, examining the body described in U.S. Pat. No. 3,778,614 radiation is directed through part of the body, from an external source, in the form of a pencil beam. A scanning movement is imposed on the beam so that it takes up in turn a large number of differing dispositions, and a detector is used to provide a measure of the absorption of the beam in each such disposition after the beam has passed through the body. So that the beam takes up these various dispositions the source and the detector are reciprocated in a plane and are orbited about an axis normal to the plane. The various dispositions thus lie in a plane through the body over which the distribution of the absorption co-efficient for the radiation used is derived by processing the beam absorption data provided by the detector. The processing is such that the finally displayed distribution of absorption is the result of successive approximations.

The method and apparatus described in the aforesaid United states patent has proved to be successful for producing cross-section representation of parts of the living body, such as the head.

In our co-pending U.S. Pat. application Ser. No. 476,300 there is described an apparatus for deriving beam absorption data in a relatively rapid manner. According to this Patent Application the derivation is achieved by directing a fan-like sheet of X-radiation through the body in the plane to be examined and providing a bank of detectors on the other side of the body to measure the radiation transmitted along a set of beam paths within the fan. The set of paths extends over an angle sufficient to include the whole region of interest in the plane of examination, so that a complete scan can be effected merely by orbiting the source of the radiation and the detectors about the body.

According to the invention from one aspect there is provided radiographic apparatus including source means arranged to irradiate a body with penetrating radiation, detector means including a plurality of detectors each arranged to detect said radiation after traversing a respective path through the body, said paths being disposed in a planar region of finite thickness, and compensating means for reducing the effect of differences between the sensitivities of the different detectors, said compensating means including displacement means for effecting relative displacement between said source means and said detector means, means arranged to receive output signals from said detectors and to utilise signals derived from successive detectors whilst the source and detector means assume first and second relative positions to predict the value of the output signals which should have been obtained from adjacent detectors and means for utilising said predicted values to compensate at least in part for differences in sensitivity between detectors.

The means for predicting the value of output signal which should have been obtained from adjacent detectors may include means for deriving signals representative of the difference of the absorption of the body under examination to radiation transmitted through the body.

Another object of the invention is to utilise difference signals in the reconstruction of the representation of the varying absorption of said planar region of the body, and according to the invention from another aspect, there is provided radiographic apparatus including source means arranged to irradiate a body with penetrating radiation, detector means arranged to detect said radiation after it has traversed said body, means for scanning said source and detector means relative to the body so as to permit the detection of radiation traversing said body along a plurality of co-planar paths, some at least of said paths being arranged to intersect one another within said body, means for processing output signals derived from said detector means, and indicative of the absorption suffered by said radiation along each of said paths (in accordance with a convolution technique) said processing means being arranged to operate upon signals representative of differences between said signals.

In order that the invention may be clearly understood and readily carried into effect, some embodiments thereof will now be described by way of example only with reference to the accompanying drawings of which:

FIG. 1a shows, in side elevation and partly in cross section, apparatus incorporating the invention, FIG. 1b is a view taken on arrow bb of FIG. 1a, FIG. 2 shows in general outline apparatus of the kind described in relation to FIGS. 1a and 1b, together with a block diagrammatic of the circuit arrangement, for performing the prediction in operation of the apparatus, FIG. 3 is a diagram illustrative of the principle of operating FIGS. 1 and 2, FIG. 4 illustrates, in cross section, an X-ray tube used in the apparatus of FIGS. 1 and 2, FIG 5 shows a detail of the tube of FIG. 4, FIG. 6 shows the tube of FIG. 4 enclosed in a suitable housing, FIG. 7 is a block diagram indicating computing circuits for producing an output representation from apparatus shown in FIG. 2;

Figure 1A:
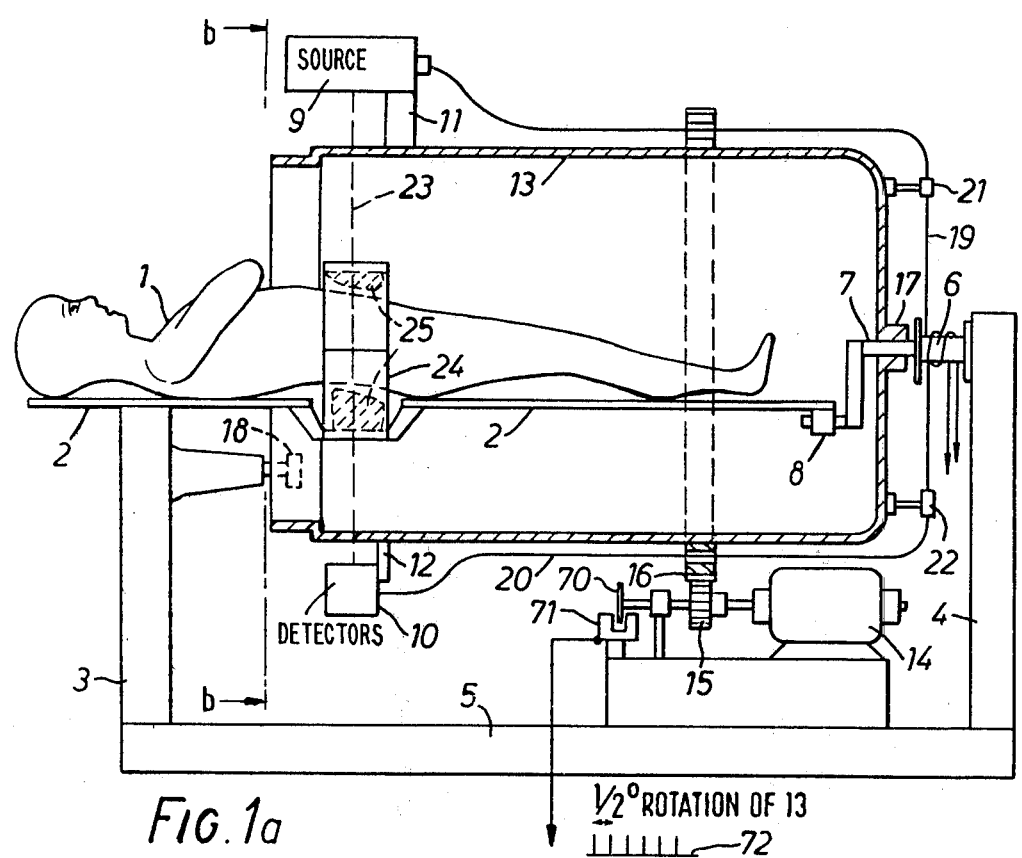
Figure 1B:
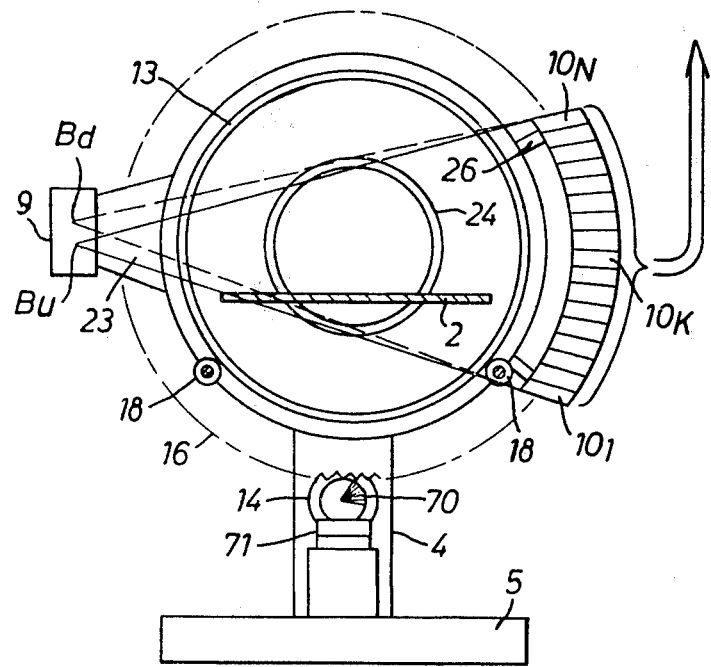

Referring now to FIGS. 1a and 1b, a body 1 to be examined is supported supine on a suitable couch 2. The couch 2 is supported at either end by respective support members 3 and 4 which are secured to a plinth 5. The support member 4 supports its end of the couch 2 indirectly via a drum 6 and an axle 7, the latter being rotatably mounted in an L-shaped member 8 which supports the couch 2.

An X-ray tube 9 and a bank of detectors 10 are mounted by respective supports 11 and 12 to the outside of a cylindrical drum 13 which surrounds part of the body 1 and is arranged to be rotated around the body by means of an electric motor 14 which drives a gear wheel 15 having teeth which engage with those of a gear ring 16 formed on the outside of the drum 13. The closed end of drum 13 carries, in its centre, a bearing 17 free to rotate on the axle 7; axle 7 being aligned with the longitudinal axis of the drum 13 and constituting the rotational axis of the system as a whole. The open end of drum 13 is supported on bearings 18, of which only one is visible in FIG. 1a, the bearings 18 being supported by the support member 3. Electrical power supplies for the X-ray tube 9 and electrical signals from the detectors are carried respectively by cables 19 and 20, and these cables are passed along the outside of drum 13 and through suitable cable guides 21, 22 respectively to the drum 6 which carries sufficient turns of the cables to allow for rotation of the drum 13 through a complete revolution thereof. It will be appreciated that because of this the drum 13 has to be returned to its initial position after the completion of each scan.

The patient is placed so that the part of his body which is to be examined is disposed in the path of the X-rays from the tube 9 to the detector 10; the tube 9 including collimator means for ensuring that the radiation is emitted in the form of a planar, fan shaped swath 23 (see especially FIG. 1b), the wide dimension of the fan being perpendicular to the plane of the paper in FIG. 1a and parallel to the plane of the paper in FIG. 1b. The region of interest of the body being investigated is surrounded by a locating ring 24 which contains packing material 25 of similar absorption characteristics to the body 1, the material 25 being tightly compressed between the ring 24 and the body 1 for the purpose of excluding, as far as possible, air from the immediate vicinity of the body.

It will be appreciated, therefore, that when the motor 14 is energised, the drum 13 will be rotated around the body carrying with it the X-ray tube 9 and the detectors 10; the fan beam 23 being therefore rotated around the body in a fixed plane so that the body is irradiated, in that plane, from a plurality of different directions.

As can be seen more clearly in FIG. 1b there are N detectors disposed opposite the tube 9, the detectors being distributed across the wide dimension of the fan beam 23. Each detector includes a collimator 26 (not individually visible) such that, if the fan beam were stationary, it would receive only such radiation as had traversed a respective linear path through the body, the width of that path being controlled by the dimensions of the collimator. In practice, the fan beam is rotated steadily around the body and because it is necessary to integrate the output signals from the detectors for a short but finite time in order to obtain reliable readings, the signals derived from a given detector relate to a path which is spread somewhat relative to the path defined by the respective collimator. The fan beam 23 may rotate through an angle of between 1° and 2° relative to the body during each finite time of integration, this angle being 1° in this example.

A typical detector comprises a scintillator crystal, disposed to receive the X-rays, which produces visible output signals in response to such radiation, the visible output signal being conveyed to a photomultiplier tube which produces an electrical output signal indicative of the amount of radiation incident on the crystal. These output signals are processed in a convenient manner so as to produce a representation of the variation of absorption, with respect to the radiation, across the plane of the body which is being investigated.

As has already been mentioned, when output signals derived from several different detectors are processed, the inherent differences in the performances of the detectors will usually give rise to undesirable patterns being superimposed on the representation.

The shape and intensity of the patterns depends to some extent upon the kind of processing used to produce the representation. In order to remove, as far as practicable, these undesirable patterns from the representation, the present invention provides for relative movement between the fan beam 23 and the detectors 10. This provides information which, given that the output signal from a given detector, the k'th say, at a given time is known, permits the calculation of what the corresponding output signal of the next adjacent detector (say the k+1'th) should be if its performance were the same as that of the k'th detector. This permits the calculated value to be compared with the actual output signal recorded at the given time by the k+1'th detector; any difference between the two compared values being assumed to be due to different performance as between the k'th and k+1'th detectors. By this means such differences can be allowed for and the undesirable patterns substantially reduced in intensity. It will be appreciated, of course, that the correction can be effected for all detectors by comparing the k'th with the k+1'th, the latter with the k+2'th, and so on.

In this example, the change of relative position between the fan beam 23 and the detectors 10 is achieved by displacing the source of the beam from position Bu in FIG. 1b to position Bd. It has previously been mentioned that the practice is to integrate detector output signals for a period corresponding to an angular rotation of the fan beam of 1° relative to the body, but when this invention is employed it is necessary to be able to separate, on a temporal basis, the output signals derived when the fan beam originates from the undisplaced (suffix u) and displaced (suffix d) positions. This can be done, for example, by keeping the fan beam in position Bu for approximately one half of the period referred to above, and then shifting the source of the beam to position Bd for the remaining half of that period. The output signals derived from the detectors during the respective half periods can be integrated separately and applied to respective stores. It will be appreciated that the steady rotation of the drum 13 proceeds undisturbed and thus it is necessary, at the end of the second half period, to return the source of the fan beam to a position corresponding to Bu, although of course the fan beam is by this time displaced from the position shown in FIG. 1b by the aforementioned angle of 1°. The procedure of displacing the source of the fan beam from one position to another and back is repeated during each 1° of the rotation.

Alternatively, it is possible to oscillate the position of the source of the fan beam more rapidly so that each position is occupied several times during the increment of angular motion. However the first embodiment of the invention to be described will assume that the technique described in the last preceding paragraph is adopted.

It will be clear from the foregoing that it is necessary for the rotation of the drum 13 around the body to be monitored accurately. In the present example this is achieved by providing a graticule in the form of opaque radial lines on a circular disc 70 of transparent material which is driven by the motor 14. The disc rotates relative to a transducer unit 71 which contains a light source and a photocell, the latter being connected to a suitable circuit of known kind to permit the generation of timing pulses 72, a pulse being provided each time the path of light to the photocell is interrupted by one of the graticule lines. The spacing of the radial lines on disc 70 is arranged so that adjacent ones of the pulses 72 are thus separated by a time equivalent to rotation of the drum 13 through $\frac{1}{2}°$.

Referring now to FIG. 2 the reference 13 denotes the drum member of a scanning or beam absorption data acquisition unit such as is described in relation to FIGS. 1a and 1b. The fan-shaped beam 23 is assumed to lie in the plane of the paper in FIG. 2, extending over the sector between the limiting rays shown as 27 and 28 and emanating from an effective point secure at Bu. The rays of the fan after passing through the body to be examined fall upon the array of detectors 10. In accordance with one aspect of the invention it is arranged as will be described to displace the relative position of the X-ray source and the array of detectors 10 so that, in a manner that will be explained, defects in the final image reconstruction of the absorption distribution in the cross-section of the body explored by the fan of radiation due to differences of sensitivity between detectors can be mitigated. As will appear, the displacement of relative position is accomplished by deflecting the exciting electron beam of an X-ray tube employed to generate the exploring radiation. Deflection of the electron beam causes the X-rays to be emitted from a patch (on the target of the X-ray tube) which differs in position from the patch which emits X-rays when the electron beam is not deflected. In FIG. 2 this patch, which is small and so amounts in effect to a point source of the radiation, is shown schematically as being displaced from the position Bu to an adjacent position Bd, the rays 27 and 28 now becoming the rays 27' and 28'. The displacement, which is not large, is shown exaggerated in the figure.

The detectors are not shown individually in FIG. 2, but as described previously each comprises a scintillation crystal, on which the radiation can impinge, the crystal being optically coupled to a photomultiplier tube; the excitation of a crystal by incident X-radiation producing light which is coupled to the respective photomultiplier tube and gives rise to an output current from the tube. The current constitutes the output current of the detector. The output currents of the various detectors flow along conductors which constitute various cores of the cable 20 (FIG. 1a) and are indicated in FIG. 2 by the general reference 29, the k'th detector feeding its output current over the conductor $29_k$ to a corresponding signal amplifier $30_k$ respective to the detector. The amplifiers 30 have individual gain adjustment means of known kind, to offset gross inequalities in the sensitivities of the detectors. Control of the gain of the amplifiers 30 is effected by means of a gain control unit 31.

The output of amplifier $30_k$ feeds into an analogue store $32_k$ which in this example is a Miller integrator of well known type. The integrator $32_k$ receives the timing impulses 72 from the timing unit 70, 71 shown as a block in FIG. 2, and each timing pulse reads and resets the integrator in known manner. The integrator circuit $32_k$ integrates the amplified output of the k'th detector successively for the aforementioned time interval corresponding to one half of the time taken for the fan beam to rotate through an angle of 1° with reference to the body. This angle of about 1° is chosen because it corresponds to the angle subtended at the source 9 by one of the detectors 10—i.e. to an effective width of the exploring beam as sensed by the detector k. In the analogue-to-digital converter $33_k$, each signal produced on resetting the integrator is changed to digital form and is fed to a log converter circuit 34 which changes the signal form to logarithmic, though still digital. The log converter circuit is common to all the converters 33. It is operated under the control of timing pulses from unit 70, 71 and withdraws in turn digital signals derived by all such converters as $33_k$ which are arranged to store the converted signals for the requisite time. In fact all the circuit functions represented by blocks in FIG. 2 from and including 34 are provided by a suitably programmed digital converter and construction details therefor are not relevant to this invention. The log converter 34 feeds the signals, duly converted to logarithmic form, to a distributor circuit 35. This last circuit passes the signals to a digital store 36 if the signal relates to position Bu of the X-ray source, or to a second digital store 37 if the corresponding position of the X-ray source is Bd. The switching pulses for controlling the distributor circuit 35 are synchronous with those of the timing circuit 70, 71 referred to above which also produces pulses for controlling the displacement of the X-ray source between positions Bu and Bd by means of a scanning circuit 73 which produces a substantially sinusoidal deflection waveform 74 for application to scanning coils 57, 58 which are referred to hereinafter in more detail and are associated with the tube 9.

As a result of the acquisition of absorption data by means of the scanning unit and with completion of an orbital scan there thus becomes stored in store 36 absorption values derived as explained and conforming to the matrix pattern:

$$R_{11}\ R_{21}\ R_{31}\ \ldots\ R_{k1}\ R_{k+1,1}\ \ldots\ R_{N1}$$
$$R_{12}\ R_{22}\ R_{32}\ \ldots\ R_{k2}\ R_{k+1,2}\ \ldots\ R_{N2}$$
$$\cdot$$
$$\cdot$$
$$\cdot$$
$$R_{1t}\ R_{2t}\ T_{3t}\ \ldots\ R_{kt}\ R_{k+1,t}\ \ldots\ R_{NT}$$
$$\cdot$$
$$\cdot$$
$$\cdot$$
$$R_{1T}\ R_{2T}\ R_{3T}\ \ldots\ R_{kT}\ R_{k+1,T}\ \ldots\ R_{NT}$$

In this array the first row corresponds to the first sampling of the fan radiation by the detector array for $\frac{1}{2}°$ rotation, the second row to the third sampling for the third $\frac{1}{2}°$ rotation the row commencing $R_{1t}$ to the sample $(2t-1)$ and the last row to the sample $(2T-1)$ which is the last sampling of the scan. The first column gives absorption values deriving from the first detector of the detector array in time order of sampling down the column, the second column those values in the same way deriving from the second detector of the detector array, and so on up to the last and N'th detector. Generically $R_{kt}$ signifies the absorption value deriving from the k th detector on the t th sampling.

Correspondingly in store 37 different absorption values are stored in an identical pattern, typical of which $R'_{kt}$ represents the value relating to the k th detector on the 2t th occasion of sampling in the displaced source position Bd. By virtue of the alternation of the source position, the value $R'_{kt}$ will have a related time of sampling intermediate those of the values $R_{kt}$ and $R_{k,t+1}$.

The block 38 represents a processing circuit which withdraws absorption data values from store in the stores 36 and 37 and uses them to derive corrected values less affected by differential detector sensitivity error than the data as held in stores 36 and 37. The corrected values are passed to a corrected data store 39. The action of the processing circuit 38 will be explained more fully. In regard to the derived data transferred to store 39 this data is processed by convolution according to any suitable technique, for example that described in U.S. Pat. No. 3,924,129 First, however, it is sorted into data relating to parallel sets of radiation paths through the body by means of a distributor circuit 40. Each such parallel set is transferred to a respective section of a parallel set store 41, these sections being n in number, n having a value rather less than the number N of detectors of the detector array.

The character of the data correction will now be explained with reference to FIG. 3. In this figure the circle C represents the orbital path of the radiation source and of the detectors of the detector array. It is assumed for the sake of simplicity that the orbital paths of the various detectors, although not necessarily the same, may be regarded as such, and the same as the orbital path of the source, and also that the array of detectors subtends at the source a comparatively small angle. The centre of the circle C, representative of the axis of the orbital rotation, is shown at O in the figure, and the undisplaced position Bu of the radiation source at the mean time of the t th sampling is also indicated in the figure. When the source is next displaced, its position at the mean time of the sampling that is then effected is shown at Bd. The figure shows radiation from the source on both occasions of sampling traversing the region of exploration and falling in each instance upon the k′th detector. Thus the path P is the path of radiation in the undisplaced position of the source and P′ that in the displaced position. In the first position the radiation path is distant OX from the orbital axis and in the second it is distant OX′.

Consider any radiation path, such as P or P′, and assume it to be distant r from the orbital axis, and to be inclined at some angle $\theta$ to a datum line in the exploring plane. Then the total absorption of radiation along it between the source and a detector, such as the k th detector, which intercepts the radiation and determines this absorption, will be a function of both mangitudes r and $\theta$. Thus if f is the absorption in actual value (as distinct from some determination of it, which latter must be inclusive of error), then f may be represented according to $$f = f(r, \theta).$$

If r is now increased by $\Delta r$, and $\theta$ by $\Delta\theta$, the value of f will increase by $$\Delta f = \frac{\partial f}{\partial r} \Delta r + \frac{\partial f}{\partial \theta} \Delta\theta.$$

This may be rewritten $$\frac{\partial f}{\partial r} = \frac{df}{dr} - \frac{\partial f}{\partial \theta} \cdot \frac{d\theta}{dr}.$$

The significance of this result is that $\partial f/\partial r$ is a quantity which, if known, permits the absorption along a path closely adjacent and parallel to a given path to be stated, assuming that along the given path to be known. The result also has the significance that it enables $\partial f/\partial r$ to be determined from data of the kind ascertained by the apparatus described with reference to FIG. 1a, 1b and 2. It thus allows the relative error in detector sensitivity to be ascertained between two such adjacent paths, as required for the more accurate operation of the apparatus, so as to reduce artificial patterns which tend to appear in the final image reconstruction due to insufficiently compensated differential sensitivities of the detectors.

Figure 3:
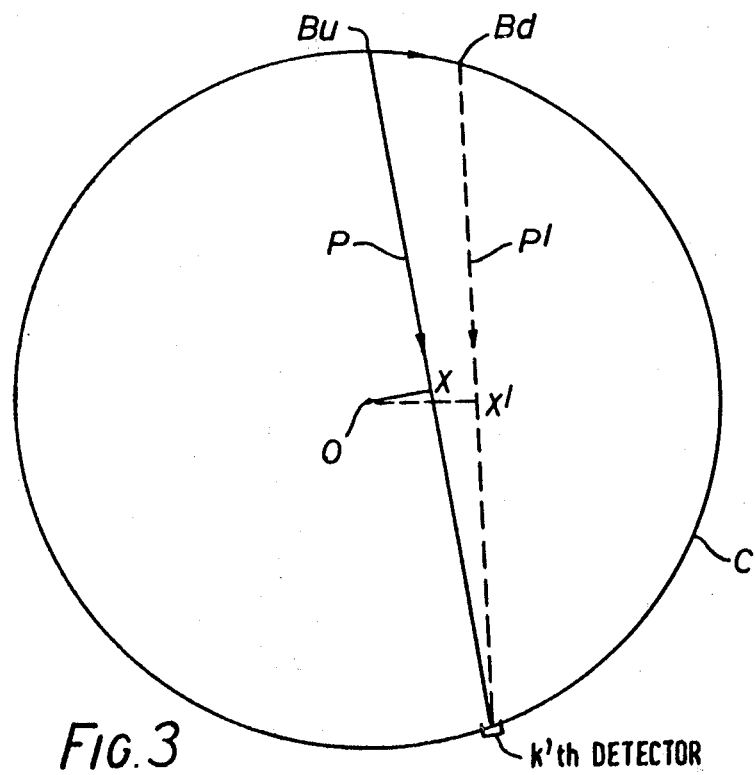

Applying these principles to the t th samplings by the k th detector, corresponding to which the value $R_{kt}$ is stored in store 36 and $R'_{kt}$ is stored in store 37, it follows that $$\left.\frac{df}{dr}\right|_{kt} = \frac{R'_{kt} + R_{kt}}{s},$$

where s is the half displacement of the source between positions Bu and Bd, in FIG. 3, namely the difference in length of the two perpendiculars OX′ and OX. Moreover, in relation to the two samplings, $$\frac{d\theta}{dr} = \frac{2s}{D} / s$$
$$= \frac{2}{D},$$

if D is the length of the paths P and P′, the lengths of which may be taken to be sensibly the same. Further if $\gamma$ is the orbital rotation occurring between the samplings to which the values $R_{kt}$ and $R_{k,t+1}$ relate then $$\left.\frac{\partial f}{\partial \theta}\right|_{kt} = \frac{R'_{k,t+1} + R_{kt}}{\alpha}.$$

These results yield $$\left.\frac{\partial f}{\partial r}\right|_{kt} = \left.\frac{df}{dr}\right|_{kt} - \left.\frac{\partial f}{\partial \theta}\right|_{kt} \frac{d\theta}{dr},$$

in which the terms on the right hand side are determined by the ascertained data in the operation of the apparatus, and in accordance with the relationships derived with respect to them.

It is thus possible to write $$R^*_{k+1,t} = R_{kt} + \left.\frac{\partial f}{\partial r}\right|_{kt} \cdot s + \left.\frac{\partial f}{\partial \theta}\right|_{kt} \cdot (\alpha - \beta)$$

giving as $R^*_{k+1,t}$ the absorption value that the (k+1)′th detector should provide on the t th sampling, if it possessed the same effective sensitivity as the k th detector. The final term contains a small correction in relation to the angle $\beta$ between the paths from the source to the k′th and (k+1)′th detectors, but if, as is usually the case, $\beta$ is sufficiently small this correction may be neglected.

Applying these methods of comparison between adjacent detectors the data of any row of absorption values, namely of any set of such values derived at any sampling time, may be corrected so that they give measured values as though the measurements were all made with effective detector sensitivities equal to the (say) of the first detector of the detector array. It is necessary, of course, that the absorption value for each detector used in correction for the next succeeding detector, shall, itself be a corrected value. The corrections have therefore to be made in sequence.

In accordance with the foregoing considerations the processor unit 38 withdraws stored absorption values held in stores 36 and 37, so that processing these values in terms of the equations derived for the partial differential coefficients of the kind $\partial f/\partial r$ and $\partial f/\partial \theta$ it computes, for every row-set of R-values held in store 36, the set of R*-values which indicate (within the limits of measurement error) the absorption determination that would have been yielded by a given detector if it had possessed the identical effective sensitivity of its neighbour. This corrected determination is applied to the store 34. The computer may however be programmed to effect correction in a different way. It will be appreciated that $$\frac{R''_{k+1,t}}{R_{k+1,t}}$$

is a measure of the sensitivity of the detector $k+1$ at time t, relative to the detector k at the same time. All these detector sensitivities may be stored. If it now can be assumed that differences of effective sensitivity of the detectors remain the same throughout the whole of a data acquisition period, a mean indication of relative sensitivities can be determined by using all row-sets of R-data. With the average values of relative effective sensitivity so made available, the R-values of store 36 can be transferred to store 39 corrected by the processor 38 in accordance with the mean relative effective sensitivity determinations.

The set of R'-values held in store 37 may likewise be corrected by either method as just described, and the corrected values used in accordance with an image reconstruction procedure identical with that by which the set of corrected R-values is processed for image reconstruction to produce a second image reconstruction which can be superposed on the first so as to establish a resultant image reconstruction with advantage against errors arising from statistical errors of data acquisition.

In circumstances in which drift of effective detector sensitivities in the course of the data acquisition period cannot be ignored, the technique of averaging relative sensitivities cannot be employed, and although the R-values can be corrected in rows, every row (in the absence of steps to the contrary) will then tend to possess an uncompensated error different from that of the other rows as a result of the drifting. Such a tendency can be mitigated by arranging that an extreme detector of the detector array measures not the absorption over a path through the body to be examined but that over a reference path. With such an arrangement the correction with respect to the reference path datum value can be made with advantage against this value averaged over brief sequence of samplings, if the drifting over this fraction of the data acquisition period is sufficiently small. Alternatively the extreme detector may be replaced by a group of such detectors of which the averaged output is employed as reference datum.

In a modification of the apparatus described with reference to FIG. 2, instead of the position of the alternated X-ray source being held fixed during the integration period in the course of which any absorption data value is built up, the X-ray source position may be alternated at a relatively high rate at the same time appropriately switching the amplified photomultiplier output signal between a pair of analogue integrator circuits respective to each detector. Each R-value with its associated R'-value corresponding to the source as displaced is thus produced simultaneously with the latter value, rather than in sequence as described in relation to FIG. 1. In the modified apparatus the R and R'-values are thus fed directly to the respective stores 36 and 37 instead of by sequential switching. The basis of correction, however, rests in the same principles. Although in this modified apparatus it is preferable that the displacement of the X-ray source should be in square-wave manner with time, the displacement may, if desired, be sinuosoidal.

It will be realised that, although it would be theoretically preferable to adopt a square-wave manner of displacement of the X-ray source rather than the sinusoidal displacement referred to previously, it may not be convenient in practice to attempt to accomplish the displacement in very strict accordance with a true square-wave displacement law. Displacement in such accordance may entail the use of harmonic deflection components which are inconveniently high multiples of the basic frequency of alternation of the source position. If such higher harmonics are not present then the transition between the alternate displacement positions will occupy a non-negligible fraction of the alternation cycle, and corresponding to this fraction the outputs of detectors will contain components that are not representative of either displacement position, but of many intermediate positions. The required corrections will not then be made with the same accuracy, but if a sufficient range of harmonics is employed corrections can be made to a satisfactory degree.

It will also be realised that deflection of the X-ray source may be accompanied by a change in emission of X-ray energy from the X-ray source. This will be compensated automatically if the X-ray emission from the source is monitored by an auxiliary detector and the outputs of the absorption sampling detectors referenced against the output of this detector.

While each of the sampling detectors is provided with collimating means to reduce errors from radiation scattered by the body under examination, it will be understood that in principle the collimation must be such as to admit of the incidence of radiation upon the scintillation crystal without discrimination between the alternating positions of the X-ray source. If in fact a degree of discrimination exists which cannot be neglected, its measure may be taken as the ratio of sums of row-sets of R-values to corresponding sums of row-sets of R'-values, this measure of discrimination then being allowed for.

With regard to the storage of values in store 39, these do not require to be values as finally corrected for detector sensitivity errors, but may be simply the corrections themselves, in the sense that the stored magnitudes of any row-set are the finally corrected values of the set less the initial reference value on which all the finally corrected values must rest. If the corrections include row-to-row correction, the whole matrix of such values is such as to yield the required image reconstruction, on image processing, short only of the mean value component. In this way the image processing can be simplified, and the image reconstruction can be completed by then adding in the appropriate mean value magnitude.

It will be understood that the principles of correction that have been enunciated, and applied to X-ray source transitions taking place in the direction from the position Bu, in FIG. 3, to the position Bd, may also be applied appropriately on the basis of transitions from the position Bd to the position Bu. Combining correction resting on both types of transition, data thereby derived from and corresponding to both R-values and R'-values may be assembled in a single matrix format in store 39 ready for image processing that is substantially free from the effects of detector sensitivity errors.

Figure 4:
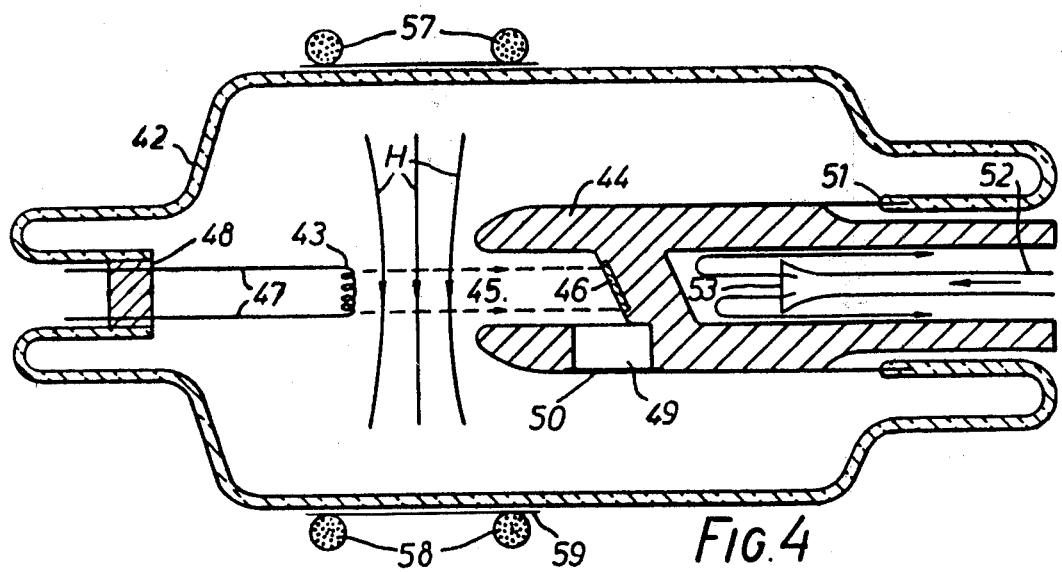

FIG. 4 shows an X-ray tube arrangement by which the relative position of the X-ray source and the radiation detectors may be alternated, the X-ray tube arrangement being devised so that its exciting electron beam can be deflected thereby to provide the alternation of relative position.

In FIG. 4 the reference 42 signifies the glass envelope of the tube. The tube cathode is indicated at 43, and 44 is an anode member. In operation exciting electrons stream from the cathode, which is held at a large negative potential, across the evacuated space of the tube as shown at 45 by the dotted lines defining the major dimension of cross section of the electron beam, to impinge on the tungsten target 46 inset in the anode member 44. This member is held at an equally large positive potential. The cathode 43 is constructed as a metal spiral of dimensions such as 2 mm. in diameter and 12 mm in length. It is supported at its ends by support wires 47, which pass through a pinch 48, and enable heating current to be applied to the spiral for the purpose of electron emission.

With bombardment of the target 46 by the high velocity electrons of the exciting stream, X-ray photons are emitted from the target in all directions. Some pass through an aperture 49 in the anode member, and a sheet of these defined as will be more fully explained constitutes the examining fan-like sheet of radiation. The aperture 49 is closed across at 50 by a suitable electrically conducting window, so that the presence of the aperture does not deform the electrostatic field required to be associated with the anode member 44.

The anode member is supported by the glass envelope 42 of the tube by a seal at 51, and is cooled more especially in the close proximity of the target 46 by cooling oil fed through a tube 52 and leaving the tube at the end 53 of the tube, this end being shaped so as to spread the flow of the cooling oil.

Figure 5:
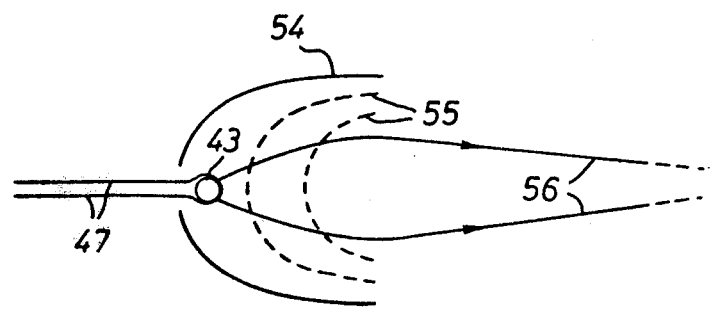

The electrons emitted from the cathode 43 are subjected to a focussing action as they stream across to the target 46, and this action is accomplished by a focussing electrode not shown in FIG. 4, but illustrated separately for convenience in FIG. 5. In this latter figure the cathode 43 is viewed from one end, such as from above in FIG. 4, and the supporting wires 47 are shown connecting with the cathode spiral. The reference 54 indicates the focussing electrode which is curved in one dimension as shown so as to be concave towards the target 46. The cathode support wires 47 pass through the electrode 54 to support the cathode close to the electrode 54 on the side of the target 46, and so that the electrode 54 is disposed in a symmetrical manner with respect to the cathode. The electrode 54 is maintained at the general cathode potential by connecting it to one of the cathode support wires 47.

The broken lines 55 show the curved character of the equipotential surfaces formed in the vicinity of the cathode 43 by reason of the focussing electrode 54. This formation results in the tracks of electrons emitted from the cathode although initially divergent being caused to become convergent. Such tracks are shown typically at 56. For the reason of this focussing action the electron beam as it impinges on the target 46 is strip like in nature. Its spread in cross section is typically 1 mm, that is to say in the plane of the paper of FIG. 5, though it extends normally to this plane over approximately 12 mm. corresponding to the length of the cathode spiral.

For the purpose of deflecting the electron beam so as to alternate the position of the effective X-ray source, a magnetic field shown at H in FIG. 4 is set up by means of deflecting currents caused to flow in the conductors of a pair of deflecting coils indicated at 57 and 58 in this figure. These coils have been referred to briefly in relation to FIG. 2, and can be of the kind such as are used with the cathode ray display tubes of television receivers, and may be simply of the so-called 'hank' variety. They are mounted on a former 59, which is slid over the envelope 42 of the tube, and disposed so that the direction of the lines of force of the magnetic field H produced when the coils are excited by a scanning waveform such as 74 from scanning circuit 73 (FIG. 2) lies essentially in the plane of the paper in FIG. 4. With this arrangement the flow of deflecting currents in the coils 57, 58 causes the electron stream to the target 46 to be deviated in a direction normal to the plane of the paper. The region of impact of the electrons on the target 46 can thus be shifted in this direction by for example 2 mm. by the application of the deflecting currents.

Figure 6:
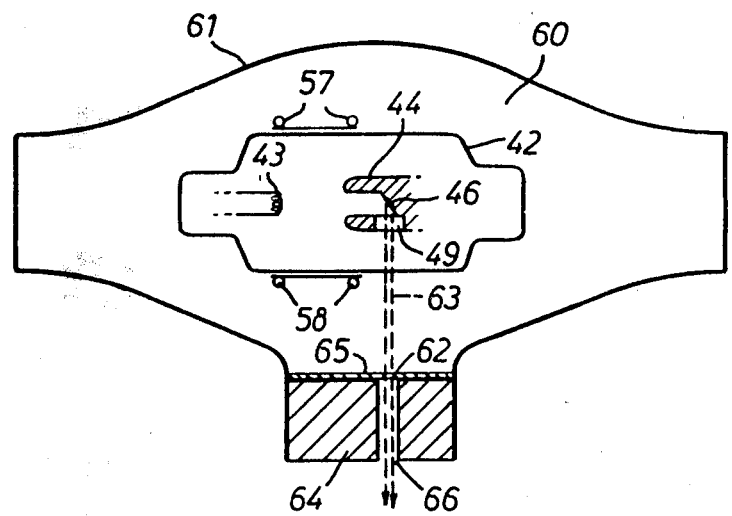

FIG. 6 depicts the tube envelope 42 immersed in cooling oil 60 which is contained within a lead lined casing 61. The lead lining may be of a thickness of 2 mm. to absorb substantially all radiation falling upon it. An aperture in the lining at 62 permits a sheet of the radiation from the target 46 to pass through the casing. This sheet is indicated in cross section by the broken lines 63, the sheet extending in a plane normal to the plane of the drawing of FIG. 6, and in the fan-like manner radiating from its source region in the target 46 that has been previously described. The cooling oil 60 is kept from passage through the aperture at 62 by means of a suitable window 65. The transmission of radiation through the aperture at 62 scattered from regions of the casing interior, and other than from the target 46, is substantially prevented by a closure in the form of a litharge bung 64. This bung does not affect the emission of the fan-like sheet of radiation as indicated at 63 by reason of the presence of a slot 66 in the bung.

Figure 7:
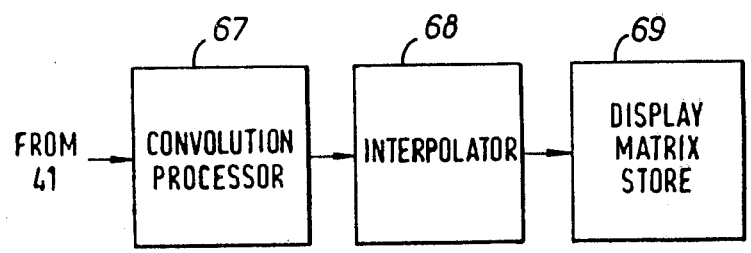

It has previously been mentioned that, rather than storing the net corrected values in the store 39 (FIG. 2) the difference between each value and a datum value (such as R11) could be stored instead and the processing performed upon these difference values. Since the difference values are already available, due to the corrective processing which has been carried out, it is convenient to utilise these difference values. In the event that the processing involves a convolution technique, it is still desirable to sort the data into parallel sets using the distributor 40 in FIG. 3, but the convolution processing itself requires some modification to enable it to cope with difference v1lues as opposed to net values. If it is assumed that the apparatus of FIG. 2 has been arranged to deposit the difference values into store 41, then those signals are applied to a convolution processing unit 67 as shown in FIG. 7 which, in its general character, may be supposed to have any appropriate form. Moreover, the data as processed by the unit 67 is subjected to an interpolation procedure subsequent to such processing. This interpolation procedure is performed in an interpolation unit 68 to which the data processed by 67 is transferred. With interpolation the data is transferred in turn to the display matrix store 69 where it is held in a form suitable for computer printout, or display by cathode ray tube, the printout or cathode ray tube display indicating the pattern of absorption over the examined cross section.

In order that the specific nature of the convolution processing performed by the unit 67 may be more clearly understood consider a function f(h) such that it represents a line integral of absorption in the plane of examination, and such that samples of it at uniformly spaced values of the parameter h represent the sequence of signals of a set fed to the store 41 in FIG. 3. It can be shown that it is possible to reconstruct the pattern of absorption in the examination plane by first of all, and in effect at least, performing the integration of the convolution.

$$\int_{-\frac{1}{2}A}^{+\frac{1}{2}A} f(h)q(r-h)dh$$

In the integral the function q is a defined convolution function and the function q may be chosen so that it imparts to the convolved data a predetermined frequency emphasis. The limits $\pm\frac{1}{2}A$ are supposed to be such as to include the whole absorption field in the integration. For convenience the integration may be split up into a large number of part integrations each covering a range equal to a sampling interval, the integration then taking on the form of a sum of a finite number of terms in which a sampled value is multiplied by an appropriate convolving factor corresponding to the part integration in question.

Figure 8:
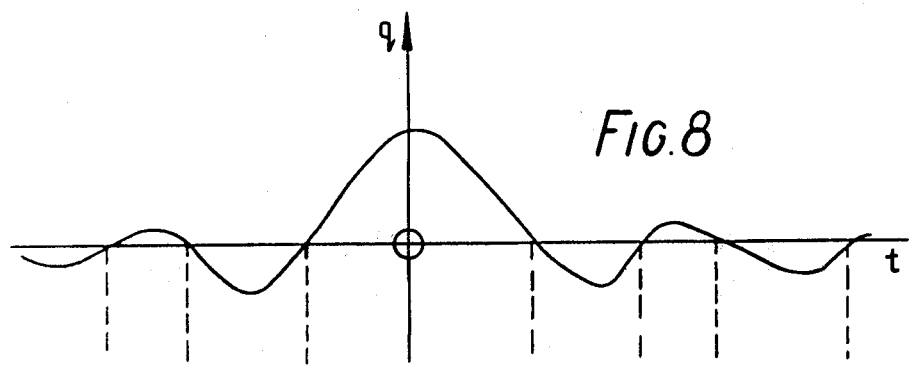
FIGS. 8 and 9 are graphs explanatory of one aspect of the invention.

FIG. 8 shows graphically the general nature of the function q(t), the analytical structure of which is such that it is an even function, and such moreover that its integral taken between the limits $\pm$ infinity is zero.

Consider p to be a function of the variable t so that for all values of t $$\frac{d}{dt} p(t) = q(t),$$

then $$q(r-h) = -\frac{d}{dh} p(r-h)$$

and writing $$C(r) = \int_{-\frac{1}{2}A}^{+\frac{1}{2}A} f(h)q(r-h)dh,$$

it follows that $$C(r) = -f(h)p(r-h)\Big|_{-\frac{1}{2}A}^{+\frac{1}{2}A} + \int_{-\frac{1}{2}A}^{+\frac{1}{2}A} f'(h)p(r-h)dh.$$

Figure 9:
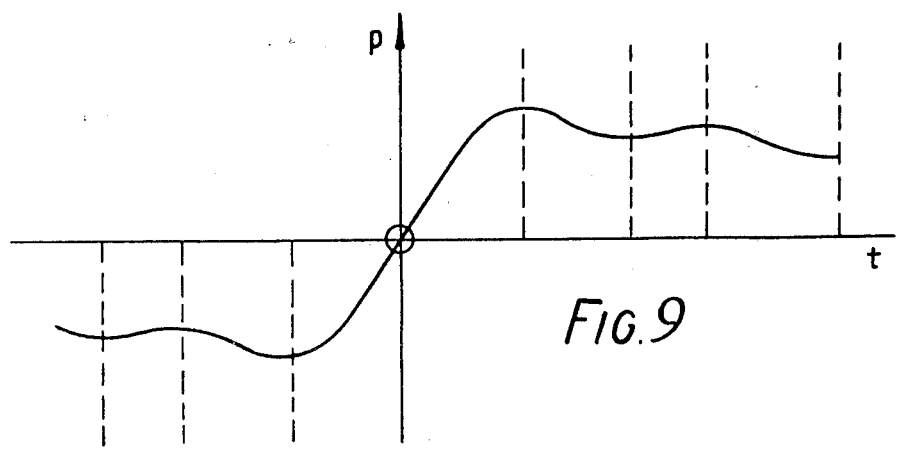

Since q is an even function and its integral is convergent as has been stated, and since the limits $\pm\frac{1}{2}A$ are assumed large enough for f(h) to converge to zero within them, it follows that the first term on the right hand side of this last equation is zero. Therefore $$C(r) = \int_{-\frac{1}{2}A}^{+\frac{1}{2}A} f'(h)p(r-h)dh,$$

in which the function p is the indefinite integral of the function q. It may be shown that any selected integral p may be augmented by any finite constant without changing the value of the convolution value C(r). In general, setting aside a constant component, the function p is an odd function, and this character is indicated in FIG. 9.

Figure 10:
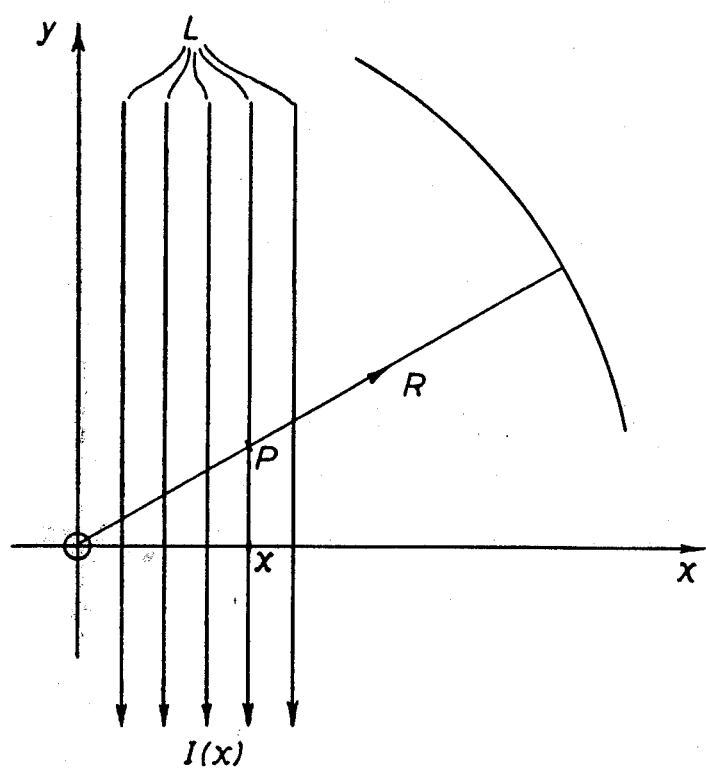
FIG. 10 is illustrative of a processing technique based on the use of difference signals as opposed to net signals.

It will be realised that the convolution integral in f'(h) may be split up into a large number of part integrals following the form of procedure of such part integration referred to so that the integral may be converted to a finite sum, each term of the sum consisting in a sampled value of f'(h) multiplied by a corresponding convolving factor determined by the form of the function p in the integration range concerned. The sampled derivative values which are samples of the function f'(h) can effectively be represented by the finite difference values referred to previously and in general may be formed in any suitable way in the context of the apparatus concerned, for example by means of the technique which will now be described with reference to FIG. 10.

This drawing may be thought of as relating to the determination of absorption coefficient at a point or points in a planar region of a body. For simplicity it is assumed that the distribution of absorption coefficients is circularly symmetrical, and that it is required to determine the coefficient at a point on the axis of symmetry. This axis is supposed to lie normally to the plane of the drawing and thus to the Cartesian axes Ox, Oy shown in FIG. 10. The lines designated L are typical of a set of parallel closely and equally spaced lines, parallel with the Oy axis, along which the total transmission of radiation is observed in each case by an appropriate measuring device. In the instance of that line distant x from the Oy axis the measured output of the corresponding device is taken to be I(x). The reference B denotes a circular bound at radius R from the origin of coordinates Q which bound is assumed to represent the edge of the body. At the point P, of which the coordinates are x,y, it is supposed that the coefficient is f(r), in which $$r^2 = x^2 + y^2.$$

In the circumstances thus presupposed it is possible to write $$I(x) = \int_{-Y}^{+Y} f(r)dy$$

where $$Y^2 = R^2 - x^2.$$

Since the relationship $$rdr = ydy$$

holds along the path of the integral, the expression for I(x) may be rewritten $$I(x) = 2 \int_{x}^{R} \frac{f(r)rdr}{(r^2 - x^2)^{\frac{1}{2}}}.$$

In this form I(x) stands as the Abel transform of f(r), corresponding to which there exists the inverse transformation $$f(r) = -\frac{1}{\pi} \int_{r}^{R} \frac{I'(x)dr}{(x^2 - r^2)^{\frac{1}{2}}}$$

in which $$I^1(x) = \frac{dI(x)}{dx}$$

Thus the coefficient on the axis of symmetry is given as $$f(O) = -\frac{1}{\pi} \int_0^R \frac{I'(x)dr}{x}$$

In finite series form assuming the spacing of the parallel paths of integration to be of sufficiently small value a, this result may be represented $$f(O) = -\frac{1}{\pi} \sum_0^N n \frac{I'(\overline{n+\frac{1}{2}}\cdot a)}{n+\frac{1}{2}}$$

or again, and in finite difference form, as $$f(O) = -\frac{1}{\pi a} \sum_0^N n \frac{\Delta(\overline{n+\frac{1}{2}}\cdot a)}{n+\frac{1}{2}}$$

in which $$\Delta(\overline{n+\frac{1}{2}}\cdot a) = I \div n + 1 \cdot a) - \check{I}(na).$$

The convolution of the derivative $I'(\overline{n+\frac{1}{2}}\cdot a)$, or the finite difference $\Delta(\overline{n+\frac{1}{2}}\cdot a)$ corresponding to it, with the function $1/(n+\frac{1}{2})$, according to the respective summations thus yields the value of the absorption coefficient at the origin. It will be evident that the restriction of a circularly symmetrical distribution may be removed if a large number of parallel sets of the observed data that has been represented by the function I(x) are derived in the first place, these sets being disposed over the range of inclination from 0 to $2\pi$ at small equi-angular spacing. On integration of the convolution sum over this angular range, asymmetrical components of the distribution to be determined suffer cancellation in anti-parallel pairs, leaving the required determination as given by the integrated convolution of the symmetrical components of the distribution. The processing technique that has been described may therefore be applied without any restriction of symmetry.

It will be realised that the finite differences formed according to the procedure that has been described will be of small magnitude compared with the values of which they are the differences. Digital multiplications of convolution can thus be accomplished in accordance with the invention in less time than those of the processing envisaged in the aforesaid specification. It will be appreciated that the apparatus described in U.S. Pat. No. 3,924,129 can be used to effect the convolution, the only change which is occasioned by the use of difference signals as opposed to net signals being that of variation of the factors referred to as L-factors in the said patent.

Although the invention has been described in relation to apparatus which examines only a single planar slice of the body at a time, it will be evident that with a suitable duplication of detectors and their associated circuits, and a modification of the shape of the X-ray beam emitted from the source 9, two or more planar slices could be examined simultaneously.

It is not necessary for the detectors to comprise individual crystals and photomultipliers. In a modified arrangement a single, large detector crystal is used, various regions thereof being coupled to respective photodetector devices.

Furthermore, although in the apparatus hereinbefore described the angle of the beam 23 of radiation has been sufficient to embrace the whole of the body in the plane of interest, this need not be the case and in a modified arrangement the tube 9 is arranged to produce a fan beam of smaller angle and a linear scanning motion is imparted to the source and the corresponding detectors relative to the body to allow proper examination of the body. This linear scanning motion is additional to the rotational scanning motion, of the source and detectors relative to the body, and the two scanning motions are synchronised.

In the example described above, the invention is used in a medical radiology machine of the type sometimes referred to as CAT scanners, in which X-radiation travels along a substantially planar slice through the patient. The X-radiation source orbits around the patient so as to send radiation along a number of directions which are at different angles to each other in the slice. The intensity of the radiation emerging from the slice is measured along each of a number of pencil-thin beam paths such that any point in the slice is traversed by a great number of such beam paths. The resulting measurements are processed, for example, as described in U.S. Pat. Nos. 3,778,614 nnd 3,924,129, to generate a picture in which each point has a brightness corresponding to the X-radiation response characteristics of the correspondingly positioned point in the slice. The picture is similar to what would be seen if the patient were cut in two along the slice and one looked at the resulting cross section through the body.

The detectors of the X-radiation are often operated near the limits of their capabilities in order to minimize the radiation dosage to the patient and to minimize the time for an examination. As a result, even small differences in the sensitivities of these several detectors may become significant and the picture may be degraded thereby. Accordingly, one aspect of the invention relates to carrying out an examination in such a way that the effect of differences between the sensitivities of the several detectors is at least reduced. In the example of the invention described above, this desired goal is accomplished by relying on changes between successive measurements taken with the detectors rather than on the absolute value of such measurements so as to obtain more accurate measurements without actually knowing what the reference line for a detector may be at any particular time.

In the specific embodiment described above, there are several detectors which are spaced along the orbiting direction and are all in the orbiting plane. One of these detectors is assumed to have an accurate sensitivity and this detector is used to provide a reading for a beam path through the patient and a reading indicating what the reading should be for an adjacent beam path. Any difference between this indication of what the reading should be for this adjacent beam path and a reading actually taken with an adjacent detector for that adjacent beam path is assumed to be due to an error in the sensitivity of the adjacent detector, and the actual readings from the adjacent detector are corrected accordingly. Once the readings for that adjacent detector are corrected as indicated above, that adjacent detector can be used to similarly correct the readings from another adjacent detector, and the procedure may be repeated for each detector in the machine. The assumption that one detector has accurate sensitivity can be accommodated even in cases where its sensitivity may in fact be incorrect because such incorrectness would reflect only (or primarily) on the overall brightness of the picture, which can be easily corrected electronically, and not on the differences between points of the picture, which is the more important characteristic of the picture.

What I claim is:

1. Radiographic apparatus including source means arranged to irradiate a body with penetrating radiation, detector means including a plurality of detectors each arranged to detect said radiation after traversing a respective path through the body, said paths being disposed in a plane of finite thickness, and compensating means for reducing the effect of differences between the sensitivites of the different detectors, said compensating means including displacement means for effecting relative displacement between said source means and said detector means, means arranged to receive output signals from said detectors and to utilise signals derived from successive detectors whilst the source and detector means assume first and second relative positions to predict the value of the output signals which should have been obtained from adjacent detectors and means for utilising said predicted values to compensate at least in part for differences in sensitivity between detectors.

2. Apparatus according to claim 1 wherein said source means comprises an X-ray tube wherein a stream of electrons is arranged to impinge upon a region of a target electrode so as to generate X-rays at the region of impingement and said displacement means comprises means for deflecting said stream on to a different region of said target electrode.

3. Apparatus according to claim 2 wherein said means for deflecting said stream comprises a pair of scanning coils mounted on the outside of said tube.

4. Radiographic apparatus including source means arranged to irradiate a body with penetrating radiation, detector means including a plurality of detectors each arranged to detect said radiation after it has traversed a respective path through the body, said paths being disposed in a plane of finite thickness, and compensating means for reducing the effect of differences between the sensitivities of the different detectors, said compensating means including displacement means for effecting relative displacement between said source means and said detector means, means arranged to receive output signals from said detectors and to utilise signals derived from a first detector whilst the source and detector means occupy first and second relative positions to predict the value of the output signal which should have been obtained from an adjacent detector, and means for comparing said predicted value with the value of the output signal actually provided by said adjacent detector to evaluate said differences in sensitivity.

5. Apparatus according to claim 2 including orbiting means for causing said source and detector means to rotate at a steady speed relative to said body around an axis perpendicular to said plane, the displacement provided by said displacement means being superimposed on said steady rotation.

6. Apparatus according to claim 2 including means for utilising a correcting signal derived from the evaluated differences in sensitivity between said first and adjacent detectors to modify output signals obtained from said adjacent detector, and for utilising the output signals so modified to evaluate a corresponding correcting signal for a further detector adjacent said adjacent detector, and for repeating these operations for all said detectors.

7. Apparatus according to claim 2 including means for storing signals related to said output signals, modified by respective correcting signals, and means for operating upon the stored signals in a predetermined sequence to effect a convolution thereof so as to generate a representation of the distribution of absorption coefficients, with respect to said radiation, across said plane.

8. Apparatus according to claim 7 wherein said means for storing is arranged to store signals indicative of the difference between each output signal and a datum signal.

9. Apparatus according to claim 2 including reference attenuating means disposed in the path of radiation from said source to at least one of said detectors, at least when the source and detector means occupy a given relative position.

* * * * *